United States Patent [19]

Ingle

[11] 4,319,583

[45] Mar. 16, 1982

[54] ANIMAL BIRTH DETECTOR

[75] Inventor: Lee E. Ingle, Douglas, Ariz.

[73] Assignee: Warren R. Jewett, Tucson, Ariz.; a part interest

[21] Appl. No.: 27,943

[22] Filed: Apr. 6, 1979

[51] Int. Cl.[3] .......... A61B 5/10

[52] U.S. Cl. .......... 128/775; 128/778; 340/573

[58] Field of Search .......... 128/774, 775, 778, 782; 340/573

[56] References Cited

U.S. PATENT DOCUMENTS

| | | | |
|---|---|---|---|
| 3,768,459 | 10/1973 | Cannon et al. | 128/775 |
| 3,844,273 | 10/1974 | Polson | 119/51 R X |
| 4,028,687 | 6/1977 | Hamaguchi et al. | 128/775 |
| 4,055,839 | 10/1977 | Skeggs | 128/775 X |
| 4,147,160 | 4/1979 | Aranow et al. | 128/775 |
| 4,232,686 | 11/1980 | Kammlade, Jr. | 128/775 |

*Primary Examiner*—Kyle L. Howell
*Attorney, Agent, or Firm*—J. Michael McClanahan

[57] ABSTRACT

An animal birth detector is described comprising apparatus attached in the proximity of the animal's vulva for detecting the birth of the animal fetus by monitoring the size of the vulva during the period prior to and during delivery of the fetus. More specifically, the animal birth detector comprises a transmitter attached to the skin proximate one side of the animal's vulva, the transmitter utilizing a reed relay switch to sense the proximity of a permanent magnet located on the opposite side of the vulva. As the vulva dilates at time of delivery of the animal fetus, the magnet is moved out of the magnetic field sensing area of the reed switch, turning on the transmitter whose transmissions are received by a receiver monitored by the stockman. The transmitter and magnet are held in place on the animal's rear section by an adhesive coated or sutured vinyl holding pad.

6 Claims, 8 Drawing Figures

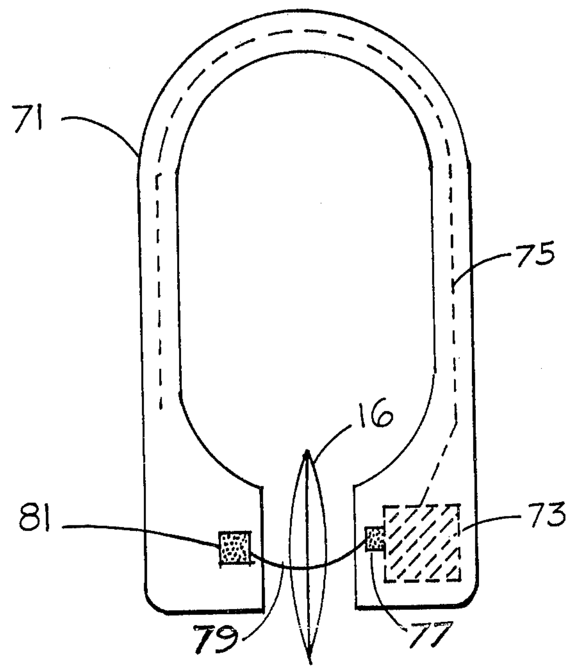
FIG. 6
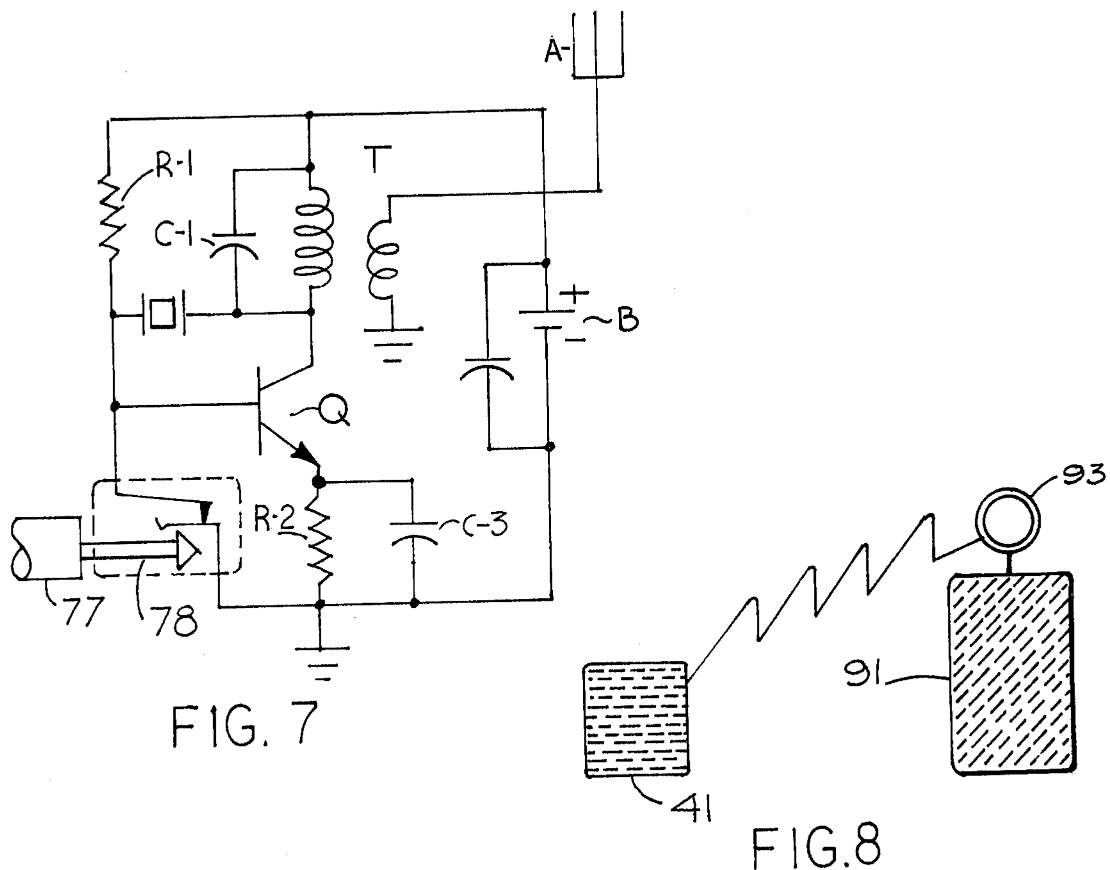
FIG. 7
FIG. 8

ANIMAL BIRTH DETECTOR

BACKGROUND OF THE INVENTION

The present invention is of the class of devices indicative that an animal is giving birth to its young.

In the past, it has been found that many times whenever horses, cattle, swine, and the like give birth to their offspring, complications tend to develop which require the aid of the stockman or the veterinarian to prevent death of the newborn or for that matter, the mother. If the animal is not penned, it is common for the animal to attempt to hide during the birthing, complicating the problem of locating the animal.

With the values which have been placed upon animals today in such cases as racehorses, milk cows, and the like, it is common for the stockman to remain close to the animal at all times during the expected period of birthing. This includes maintaining an all night vigil.

Obviously then, it is to a stockman's advantage to know exactly when, and if necessary, where an animal is in the process of birthing its young. It is to the detection of the birth of the animal fetus that this invention is directed.

SUMMARY OF THE INVENTION

The present invention comprises an animal birth detector for mounting proximate the animal's vulva whereby a contained transmitter may emit a signal to an awaiting transmitter to indicate that the animal is actually in the process of birthing the fetus. More specifically, the size of the animal's vulva is monitored by sensing its diameter during the process of dilation and when the diameter exceeds a specified distance indicative of birth, the transmitter is energized. The means by which the width of the vulva is sensed comprises a transmitter circuit having a reed relay switch in its circuitry. The reed relay switch is located as near one side of the vulva as possible and the sensed bar magnet is located on the other side of the vulva. Once the bar magnet has passed out of the sensing area of the reed relay switch so that the magnet's magnetic field is no longer closing the switch, the switch opens which in turn energizes the transmitter which commences transmitting its signal.

The stockman, who is monitoring a receiver, picks up the transmitted signal. The frequency of the transmitted signal is such that a direction finding antenna may be utilized in combination with the receiver to point the general direction in which the animal is located, if the animal is not penned. The stockman then may seek out the animal and ascertain that the fetus and the mother are in satisfactory condition.

The transmitter and the bar magnet are held in proximity to the animal's vulva by adhesive coated or suture attached vinyl pads which are adapted to hold the transmitter and magnet in pouches formed therein. An adhesive release strip is pulled from the adhesive coated side of the vinyl pad and after the appropriate area on the rear of the animal has been cleansed, the pad is adhered to the animal's skin in position. Means are also provided to permit the suturing of the pad in place upon the animal's rear section.

Accordingly, it is an object of the subject invention to provide a means to detect the birth of an animal fetus.

It is another object of the subject invention to provide apparatus detecting the dilation of an animal's vulva.

It is a further object of the subject invention to provide apparatus by which the location of an animal birthing a fetus may be determined.

BRIEF DESCRIPTION OF THE DRAWINGS

FIG. 6 is a partial front view of the rear section of an animal with a second alternate embodiment of the invention in place.

FIG. 7 is the electrical schematic diagram of the second alternate embodiment of the invention.

FIG. 8 is a functional block diagram of the invention in combination with a receiver and direction finder.

DETAILED DESCRIPTION OF THE PREFERRED EMBODIMENT

Figure 1:
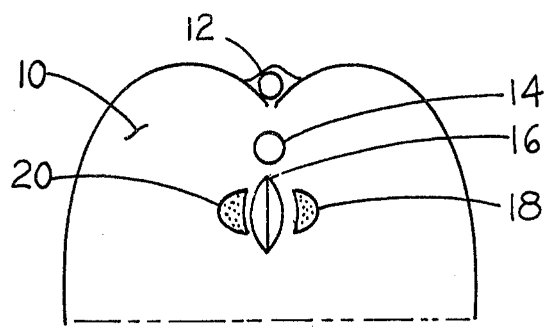
FIG. 1 is a simplified front view of the rear section of an animal showing the invention in place.

Referring to FIG. 1, the preferred embodiment of the animal birth detector is shown in position proximate the animal's vulva. More specifically, the rear section 10 of the animal upon which the birth is anticipated is defined, showing tail 12, anus 14 and the animal's vulva 16. On opposite sides of the vulva, in close proximity thereto, is placed the subject invention comprising the transmitter portion 18 of the birth detector and the complimentary magnet holding portion 20 on the vulva opposite side.

Since it is intended that the invention should indicate the actual birth of the animal, it is desirable that the invention not indicate flexations of the vulva which are preliminary to the actual birth or delivery of the fetus. For the larger animals such as horses and cows, an indication of when the vulva opening has approached a separation through the center of three or more inches is generally indicative of actual birth. It is desirable that the birth indicator be as close to the sides of the vulva as possible and in the preferred embodiment, the birth detector will then indicate when the vulva separation approaches three inches or so. At this time, the transmitter reed relay switch will be about four inches from the bar magnet, the outer edge of the reed relay sensing area.

Figure 2:
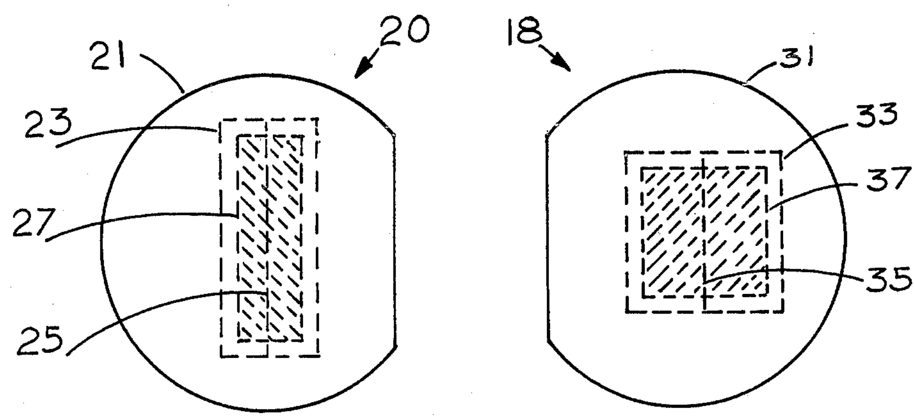
FIG. 2 is an expanded top view of the invention.

Referring now to FIG. 2, an expanded drawing of the subject transmitter portion 18 and magnet holding portion 20 is shown. Upon the outside and holding the transmitter in place is a flexible flat material 31 pad, such as vinyl, to which has been applied an adhesive, such as the type that is used for colostmy patients. In particular, 3M Ostomy Seal has been utilized. The adhesive is applied to the underside of the flexible material pad and normally has a removable cover strip exposing the sticky adhesive. Built-in between the least two layers of flexible material pad 31 is pouch 33 to which access is gained from the bottom, i.e., the adhesive side, by means of slit 35. Placed internally to pouch 33 through the access provided by slit 35 is transmitter wafer 37, which is defined supra.

On the opposite side of FIG. 2 is the magnet holding portion 20 which, like its transmitter portion 18 counterpart, comprises flexible layered material pad 21, which is also backed by the same or similar adhesive material as was transmitter portion 18. Defined between at least two layers of the material pad 21 is pouch 23 into which access is gained through slit 25, the slit being through the bottom layer of material pad 21 covered with the adhesive. Internal to pouch 23 is held bar magnet 27.

In installation of the subject invention surrounding the animal's vulva, it is anticipated that two fresh pads of the flexible materials 21 and 31 will be obtained, the transmitter wafer and the bar magnet slipped into their respective pouches (the adhesive covering release strip also having a slit therethrough aligned with the primary slit through the lower pad material layer), the adhesive release cover removed, and the pads then placed upon the animal's skin proximate the vulva.

It is suggested that the skin surrounding the vulva shall be cleansed with a cleaning material, such as warm soapy water, rinsed and dried. If excess hair is present which might interfere with the adhesion of the pads to the skin, it may be necessary to clip or shave this hair off. It is also suggested that tincture of benzoine will be applied to the area where the pads will be placed prior to the placement of the pads thereon. This is for the purpose of making the area antiseptic prior to the placement.

The pads then are placed as close as possible to the vulva without obstructing the vulva opening.

Figure 3:
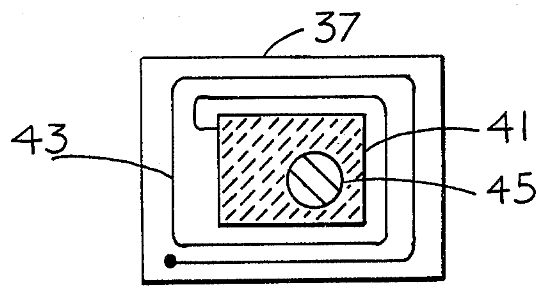
FIG. 3 is a top view of the transmitter wafer.

Proceeding now to FIG. 3 a top view of the transmitter wafer 37 is shown. Located upon the wafer material is the transmitter module 41 surrounded by its spiraling antenna 43. The transmitter module 41 is firmly attached to transmitter wafer 37 by means of an adhesive and antenna 43 is a wire which is also secured to transmitter wafer 37 by an adhesive. It is anticipated that the transmitter electronic circuit shall be inside transmitter module 41, a small container, for purposes of safety or to prevent the components from being knocked off or apart. The transmitter is powered by a small electric battery which, in the preferred embodiment, is of the same type used with cameras and which is inserted into the transmitter module through means of threaded disc 45 (its periphery being threaded) which has a central slot cut therein so it may be removed or re-inserted by a coin. This type of cover for an internally held battery is well-known in the camera art.

It is anticipated that the transmitter wafer 37 will be constructed out of bakelite, plastic, or other similar material. Naturally, it is desired that the thickness of the transmitter wafer 37 plus the attached transmitter module 41 be kept at a minimum since this is going to represent a protrusion extending from the skin of the animal and resistance to being knocked or rubbed off by the animal is highly desirable.

Figure 4:
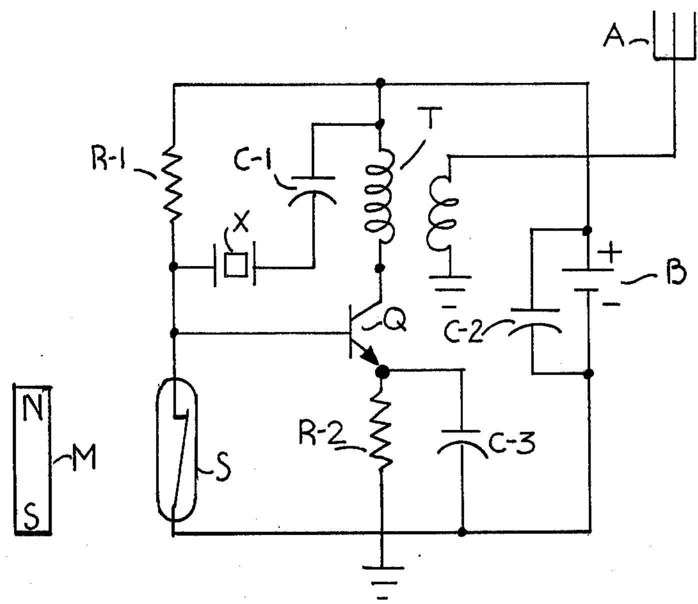
FIG. 4 is an electrical schematic diagram of the transmitter.

FIG. 4 is an electrical schematic diagram of the transmitter which is of ordinary design and is contained within transmitter module 41. The construction and operation of the transmitter is well-known in the art and operation will not be discussed other than to state that the transmitter is commonly known as a low power transmitter, frequency crystal controlled, and which is energized so as to commence transmitting a signal upon the opening of switch S.

Switch S is a reed relay switch which, in the presence of magnet M, (not a portion of the transmitter module), closes and thus inhibits signal transmission. Upon the removal of magnet M from the proximity of reed switch S, the contact interior to switch S opens and the transmitter commences its transmission. Since the reed switch S is a magnetic field proximity device, it has been determined for the components which are utilized in the preferred embodiment and whose identification is listed at the end hereof, that when the magnet is more than about four inches from reed switch S, the reed switch S does not respond to the now distant magnetic field and then opens.

The reed switch S is located inside the transmitter module covering, which in the preferred embodiment is made of thin sheet metal. It has been determined that it does not make an appreciable difference whether the transmitter module covering is metal or non-metallic.

The above transmitter functioning is the case for the actual birth of the fetal animal. However, in the alternative, should the animal succeed in rubbing or knocking off either one of the two vinyl pads, the transmitter would also commence to transmit its signal. This informs the stockman or operator who is monitoring a receiver for the signal that the animal is giving birth or has succeeded in knocking off the birth detector.

Now it is known that for different types of animals, different and alternate embodiments of the invention best serve the purpose of indicating birth. This is because the animal is known to be of a type that might rub off the invention, or that the area surrounding the vulva is constructed such that any addition atop the skin would be susceptible to being knocked off. To this end, the Applicant has devised other embodiments to remedy these problems.

Figure 5:
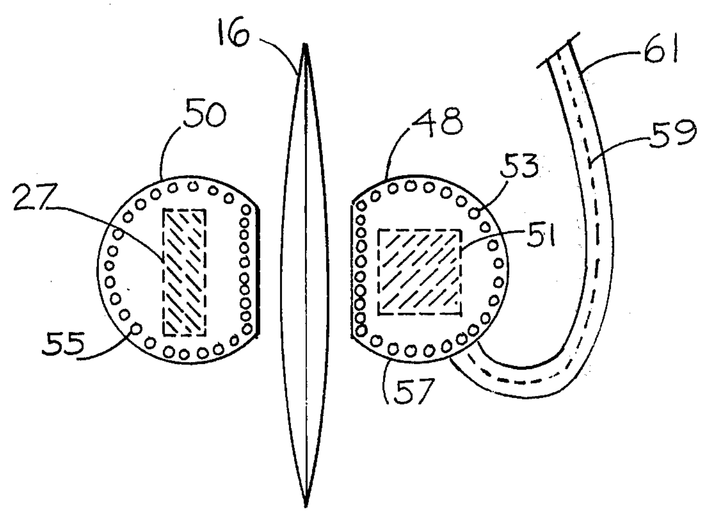
FIG. 5 is a partial front view of the rear section of an animal with a first alternate embodiment of the invention in place.

More specifically, and with reference to FIG. 5, a portion of the rear section of an animal is shown where, surrounding vulva 16 are the two vinyl pads, the transmitter portion pad 48 and the magnet receiving pad 50. However, there are two significant differences in these embodiments, namely that the pads 48 and 50 are sutured to the skin of the animal proximate the vulva, and holes for receiving the sutures are shown on the periphery of the pads, these being holes 53 and 55. As an example, shown emitting from two holes 53 of pad 48 are suture materials 57 which have formed a loop under the skin of the animal and which ends shall be tied.

The other significant difference is that shown in dotted form extending from transmitter module 51, namely antenna 59 which traces its path from transmitter 51 through the slit in the layer of material of pad 48 proximate the animal's skin, and continuing to the area of the animal near the pads, being covered by an adhesive tape or other similar type of material. It is anticipated that with this construction of antenna, greater range may be obtained.

Thus, if the removal of the pads from the animal's rear section is anticipated to be done by the animal, suture means are available to adhere the pads to the animal's skin. Of course, the adhesive material may also be placed upon the portion of the pad proximate the animal's skin.

In preparing the animal for the application of the embodiment shown in FIG. 5 it is suggested that after the area has been cleansed, lydocaine be injected under the skin to numb the skin for the suture stitching.

A second alternate embodiment of the preferred embodiment is shown in FIG. 6 where all portions of the invention have been combined on one adhesive coated pad 71. Here, as in FIG. 5, the transmitter 73 has extending from it antenna 75 which is covered by the adhesive coated pad. Now rather than depending upon proximity of a magnet to close a reed relay switch, a miniature telephone type jack 77 is attached to wire 79 which in turn is attached to one side of the adhesive coated patch by a stay 81, with the jack terminal penetrating to a jack receptacle (not shown) inside the interior of the container holding transmitter 73. Here, as the vulva expands during the birth and its width has exceeded the built-in slack of wire 79, jack 77 is pulled from its female receptacle interior to and wired in transmitter 73 circuitry, permitting the breaking of a circuit therein (FIG. 7) and commencing transmission of signals from transmitter 73.

Reference now to FIG. 7, the basic transmitter circuit shown in FIG. 4 is repeated with the exception that the former reed switch S has been replaced with the female receptacle for telephone jack 77. In this configuration, when the male portion 78 of jack 77 is removed from the female receptacle, the contacts therein are permitted to separate. This allows the transmitter to commence transmission. For simplicity, the female receptacle which receives jack 77 has been shown in dotted form in order that the electrical connections interiorly may be illustrated.

Of course, the inverted "U" shaped pad of the second alternate embodiment may be sutured to the animal's skin, as well as, for that matter, the preferred embodiment.

In order to accomplish the invention described herein, the following components have been utilized in its construction: R1, 47 K ohm; R2, 560 ohm; C1, 36 pf; C2, C3, 1000 pf; B, 1.5 volt, S-13 Eveready battery; T, sub-miniature, 16 turn (C-1 side), 2 turn (antenna side); Q, MMT 74, Motorola; S, reed switch, mini-25-11S, Hamlin; M, magnet ¼ inch by 1 inch, Samarium-Cobalt alloy; X, quartz crystal, 49.850 MHz, SC45, Sentry Manufacturing Co., Chickasha, Okla.; jack 77 and jack receptacle 83, Switchcraft, subminiature phone jack and jack receptacle.

Referring now to FIG. 8, a schematic block diagram is shown of the subject transmitter used in combination with a direction finding receiver. This is utilized when the animal is not penned and may be within a relatively large area, but still within the range of the receiver. Here, because of the relatively high frequency which is employed in the transmitter, direction finding is possible. Referring specifically to FIG. 8, the receiver 91 is electrically connected to the mechanically directed direction finding antenna 93 which picks up the transmitted signals from the transmitter module 41. By this means, the general direction of the animal may be located since, as earlier mentioned, the animals have a tendency to hide when birthing.

It is noted that in the event that more than one animal is birthing and it is necessary to monitor all of them, frequencies which are employed by the crystal controlled transmitters may be varied so that it may be determined which animal is in fact in the process of giving birth. In addition, an oscillator in the audio range may be attached to the transmitter such as to frequency modulate the crystal controlled transmitter frequencies which, when employed, may be detected by an FM receiver in order that birthing may be detected among certain selectively located animals.

Since it is anticipated that the subject invention may be used on a great number of animals such as cows, horses, zoo animals, and game animals, it may be necessary to choose which of the embodiments is best suited, or which device is best suited for any one particular animal out of the same group. For example, when using upon horses, the extension or depression of the vulva will help decide which method is best. If the vulva is depressed and of relatively large size, the preferred embodiment may fulfill all the requirements. However, if the vulva is small, extended, or flat against the rump, where the pads may be rubbed or knocked off, it may be necessary to suture the pads to the animals's skin. In addition, if the animal is to be at extended range from the receiver, the larger antenna of the second alternate embodiment is best suited.

In experiments utilizing the subject invention, is has been best determined that the invention be attached to the animal 12 days to 2 months prior to the expected birth. Current drain on the battery utilized with the transmitter is minimal except during periods of transmission and long life may be expected from these batteries.

While the preferred embodiment has been shown and described, together with two alternate embodiments, it would be understood that there is no intent to limit the invention by such disclosure, but rather it is intended to cover all modifications and alternate constructions falling within the spirit and the scope of the invention as defined in the appended claims.

I claim:

1. A device for detecting fetal birth in animals by monitoring vulva separation comprising:

a two-part non-operably connected vulva separation detection means adapted to be attached on opposite sides proximate the animal's vulva, said vulva separation means defining means sensing proximity of one side of the vulva to the other, and signal transmission means operably connected to said vulva separation detection means whereby when the animal's vulva separates, the vulva separation detection means senses separation of one side of the vulva from the other and the signal transmission means transmits such occurrence.

2. The device for detecting fetal birth in animals as defined in claim 1 wherein said vulva separation detection means proximity sensing means comprises a first part magnetic field generation means adapted to be attached to one side of an animal's vulva and a second part magnetic field sensing means adapted to be attached to the other side of the animal's vulva whereby when the magnetic field sensing means detects a predetermined reduced magnetic field strength due to separation of the animal's vulva indicating birth is occuring, said transmission means transmits a signal indicating the birth.

3. The device for detecting fetal birth in animals as defined in claim 2 wherein said magnetic field generation means defines permanent magnet means and said magnetic field sensing means defines reed relay switch means.

4. The device for detecting fetal birth in animals as defined in claim 3 wherein said signal transmission means defines radio signal transmitter means.

5. The device for detecting fetal birth in animals as defined in claim 1 further including radio receiver means for indicating the reception of the radio signal from said signal transmission means whereby when the animal birth is detected and signal transmitted, said radio receiver indicates the birth.

6. The device for detecting fetal birth in animals as defined in claim 5 wherein said signal receiving means comprises directional signal receiving means whereby the direction of the birthing animal may be determined.

* * * * *